United States Patent [19]

VandenBerg

[11] Patent Number: Plant 7,632

[45] Date of Patent: Aug. 27, 1991

[54] CHRYSANTHEMUM PLANT NAMED DARK GRENADINE

[75] Inventor: Cornelis P. VandenBerg, Salinas, Calif.

[73] Assignee: Yoder Brothers, Inc., Barberton, Ohio

[21] Appl. No.: 481,066

[22] Filed: Feb. 16, 1990

[51] Int. Cl.[5] ..... A01H 5/00

[52] U.S. Cl. ..... Plt./82

[58] Field of Search ..... Plt./76, 79, 82

[56] References Cited

U.S. PATENT DOCUMENTS

| | | | |
|---|---|---|---|
| P.P. 5,338 | 11/1984 | Meek et al. | Plt. 76 |
| P.P. 5,447 | 4/1985 | Duffett et al. | Plt. 82 |
| P.P. 6,938 | 7/1989 | VandenBerg | Plt. 82 |
| 4,616,099 | 10/1986 | Sparkes | 800/1 |

OTHER PUBLICATIONS

Gosling, ed. 1979, *The Chrysanthemum Manual*-6th edition of the National Chrysanthemum Society, Essex Telegraph Press, Ltd., England, pp. 329-336.

Broertjes et al, 1980, "A Mutant of a Mutant of a mutant of a . . . Irradiation of Progressive Radiation-Induced Mutants in a Mutation Breeding Programme with *Chrysanthemum morifolium*", Euphytica 29: 525-530.

Broertjes et al. 1978, *Application of Mutation Breeding Methods in the Improvement of Vegetatively Propagated Crops*, Elsevier Sci. Pub. Co., New York, pp. 162-175.

Searle et al. 1968, *Chrysanthemums the Year Round*, Blandford Press Ltd., London, pp. 27-29, 321-327.

Broertjes, 1966, "Mutation Breeding of Chrysanthemums", Euphytica 15: 156-162.

Dowrick, 1965, "The Induction of Mutations in Chrysanthemum Using X- and Gamma Radiation", Euphytica 15: 204-210.

Chan, 1966, "Chrysanthemum and Rose Mutations Induced by X-Rays", Amer. Soc. Hort. Sci., vol. 88: 613-620.

*Primary Examiner*—Howard J. Locker

*Attorney, Agent, or Firm*—Foley & Lardner

[57] ABSTRACT

A Chrysanthemum plant named Dark Grenadine particularly characterized by its flat capitulum form; decorative capitulum type; coral-red ray floret color; diameter across face of capitulum of 69 to 75 mm when fully opened; plant height of 33 to 46 cm at time of flowering, based on June 15 planting under natural daylength in Hightstown, N.J.; spreading branching pattern; average natural season flower date of August 31 in Salinas, Calif. and September 27 in Hightstown, N.J.; flowering response in photoperiodic controlled flowering programs of 49 to 54 days after start of short days; and durable, uniform performance.

3 Drawing Sheets

The present invention comprises a new and distinct cultivar of Chrysanthemum, botanically known as *Dendranthema grandiflora*, and referred to by the cultivar name Dark Grenadine.

Dark Grenadine, identified as 77-463B04, is a product of a mutation induction program. The new cultivar was discovered and selected by Cornelis P. VandenBerg on Sept. 7, 1984 in a controlled environment in Salinas, Calif. as one flowering plant within a flowering block established as rooted cuttings from stock plants which had been exposed as unrooted cuttings to an X-ray source of 1,750 rads. The irradiated parent cultivar was Grenadine, a coral-bronze flat decorative garden mum, disclosed in U.S. Plant Pat. No. 5,338.

The first act of asexual reproduction of Dark Grenadine was accomplished when vegetative cuttings were taken from the initial selection in November 1984 in a controlled environment in Salinas, Calif., by technicians working under the supervision of Cornelis P. VandenBerg.

Horticultural examination of controlled flowerings of successive plantings has shown that the unique combination of characteristics as herein disclosed for Dark Grenadine are firmly fixed and are retained through successive generations of asexual reproduction.

Dark Grenadine has not been observed under all possible environmental conditions. The phenotype may vary significantly with variations in environment such as temperature, light intensity and daylength.

The following observations, measurements and comparisons describe plants grown in controlled open areas in Salinas, Calif. and in Hightstown, N.J., and photoperiodic controlled programs conducted in Salinas, Calif.

The following traits have been repeatedly observed and are determined to be basic characteristics of Dark Grenadine, which, in combination, distinguish this Chrysanthemum as a new and distinct cultivar:

1. Flat capitulum form.
2. Decorative capitulum type.
3. Coral-red ray floret color.
4. Diameter across face of capitulum of 69 to 75 mm when fully open.
5. Plant height ranging from 33 to 46 cm from soil line at time of flowering, based on June 15 planting under natural daylength in Hightstown, N.J.
6. Spreading branching pattern, with an average of 7 to 8 branches per plant after pinch two weeks after planting a rooted cutting in Hightstown, N.J.
7. Average natural season flower date of August 31 in Salinas, Calif. and September 27 in Hightstown, N.J., based on several years of trial flowering.
8. Flowering response in photoperiodic controlled flowering programs of 49 to 54 days after start of short days.
9. Durable, uniform performance.

The accompanying photographic drawings show typical inflorescence and leaf characteristics of Dark Grenadine, with the colors being as nearly true as possible with illustrations of this type.

Sheet 1 is a color photograph of Dark Grenadine grown as a pinched pot mum in a 15 cm pot.

Sheet 2 is a black and white photograph of three views of the inflorescence of Dark Grenadine.

Sheet 3 is a black and white photograph showing the upper and under sides of the leaves of Dark Grenadine at three stages of development (mature, intermediate and immature).

Of the commercial cultivars known to the inventor, the most similar in comparison to Dark Grenadine is the parent cultivar Grenadine. All traits of Dark Grenadine are similar to those of Grenadine, except the color of ray florets. The color of the ray florets of Dark Grenadine is a unique coral-red, darker than the color of Grenadine, which is described as coral-bronze and identified in the noted plant patent by the color values 182C oxidizing to 182D and 181D on the upper ray floret surface. The color of Dark Grenadine has a substantially greater red tone, resulting in the respective cultivars having a distinctly different color impression.

In the following description color references are made to the Royal Horticultural Society Colour Chart. The actual color of Dark Grenadine is not represented in the R.H.S. Colour Chart, and the values given are those closest to the actual color of Dark Grenadine. The color values were determined on plant material grown as a pinched spray pot mum in Salinas, Calif. on Sept. 19, 1989.

Classification:

*Botanical.*—*Dendranthema grandiflora* cv Dark Grenadine.

*Commercial.*—Decorative spray pot mum and garden mum.

INFLORESCENCE

A. Capitulum:

*Form.*—Flat.

*Type.*—Decorative.

*Diameter across face.*—69 to 75 mm when fully open.

B. Corolla of ray florets:

*Color (general tonality from a distance of three meters).*—Coral-red.

*Color (upper surface).*—Closest to 179A, fading to 179B.

*Color (under surface).*—Closest to 179C.

*Shape.*—Straight, oblong.

C. Corolla of disc florets:

*Color (mature).*—14A.

*Color (immature).*—2A. Very few disc florets, covered by inner rows of ray florets. Under certain conditions disc florets are not present.

D. Reproductive organs:

*Androecium.*—Present on disc florets only, very few; scant pollen.

*Gynoecium.*—Present on both ray and disc florets.

PLANT

A. General appearance:

*Height.*—Ranging from 33 to 46 cm from soil line at time of flowering, based on June 15 planting under natural daylength in Hightstown, N.J.

*Branching pattern.*—Spreading.

B. Foliage:

*Color (upper surface).*—147A.

*Color (under surface).*—147B.

*Shape.*—See photograph.

I claim:

1. A new and distinct Chrysanthemum plant named Dark Grenadine, as described and illustrated.

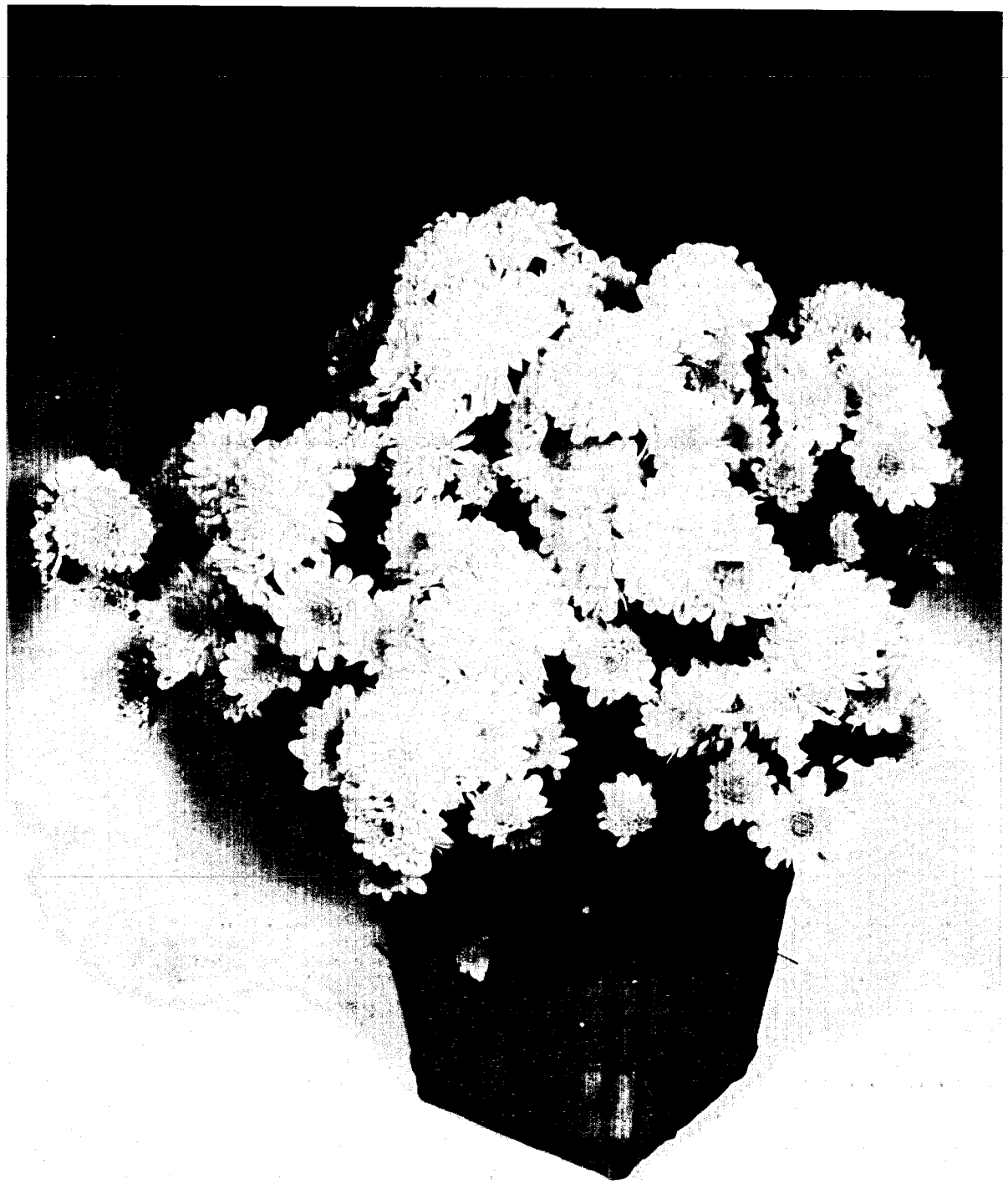

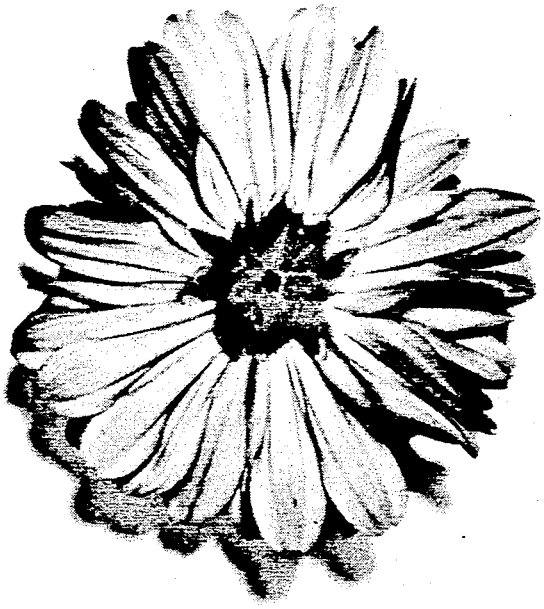
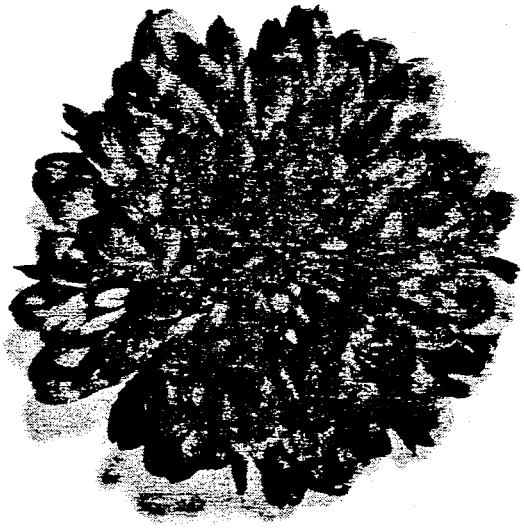
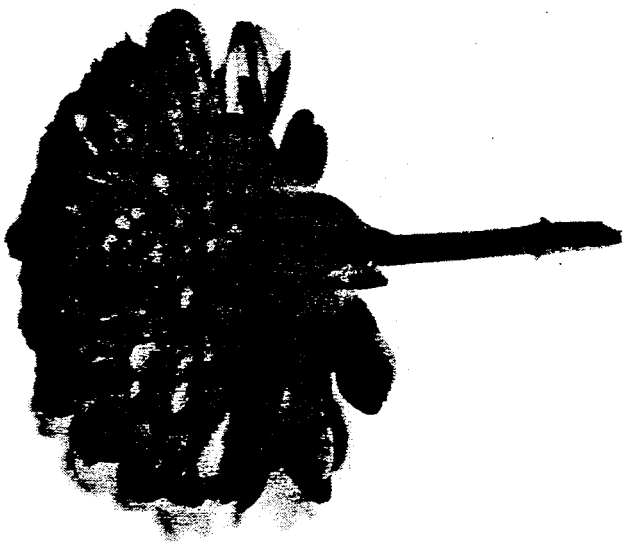

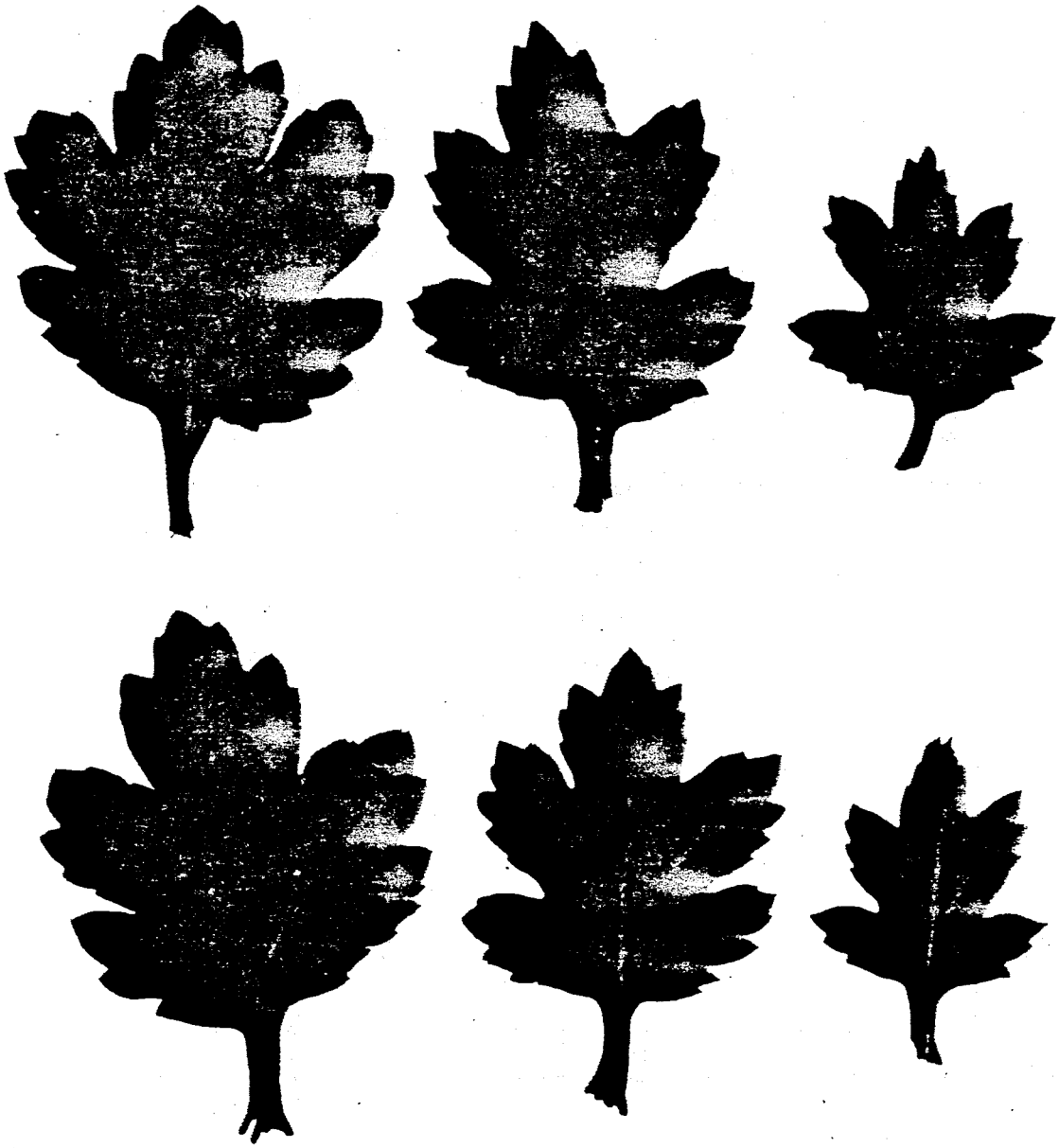

* * * * *